US00PP35183P2

(12) United States Plant Patent
Trees

(10) Patent No.: US PP35,183 P2
(45) Date of Patent: May 23, 2023

(54) ***LEUCANTHEMUM* PLANT NAMED 'SUNRIMAIAPY'**

(50) Latin Name: ***Leucanthemum* x *superbum***
Varietal Denomination: Sunrimaiapy

(71) Applicant: SUNRISE FARM FLOWERS, LLC, Arroyo Grande, CA (US)

(72) Inventor: Scott C. Trees, Arroyo Grande, CA (US)

(73) Assignee: SUNRISE FARM FLOWERS, LLC, Arroyo Grande, CA (US)

( * ) Notice: Subject to any disclaimer, the term of this patent is extended or adjusted under 35 U.S.C. 154(b) by 0 days.

(21) Appl. No.: 17/895,939

(22) Filed: Aug. 25, 2022

(51) Int. Cl.
*A01H 5/02* (2018.01)
*A01H 6/14* (2018.01)

(52) U.S. Cl.
USPC ..... Plt./285
CPC ..... *A01H 6/14* (2018.05)

(58) Field of Classification Search
USPC ..... Plt./285
CPC ..... A01H 6/14; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Leucanthemum* plant named 'Sunrimaiapy', characterized by its relatively compact, upright and mounded plant habit; freely branching habit; strong flowering stems; early and freely flowering habit; long flowering period; large single-type inflorescences with white-colored ray florets and bright yellow-colored disc florets; no vernalization requirement for flowering; good garden performance and winter hardiness.

2 Drawing Sheets

Figure 1:
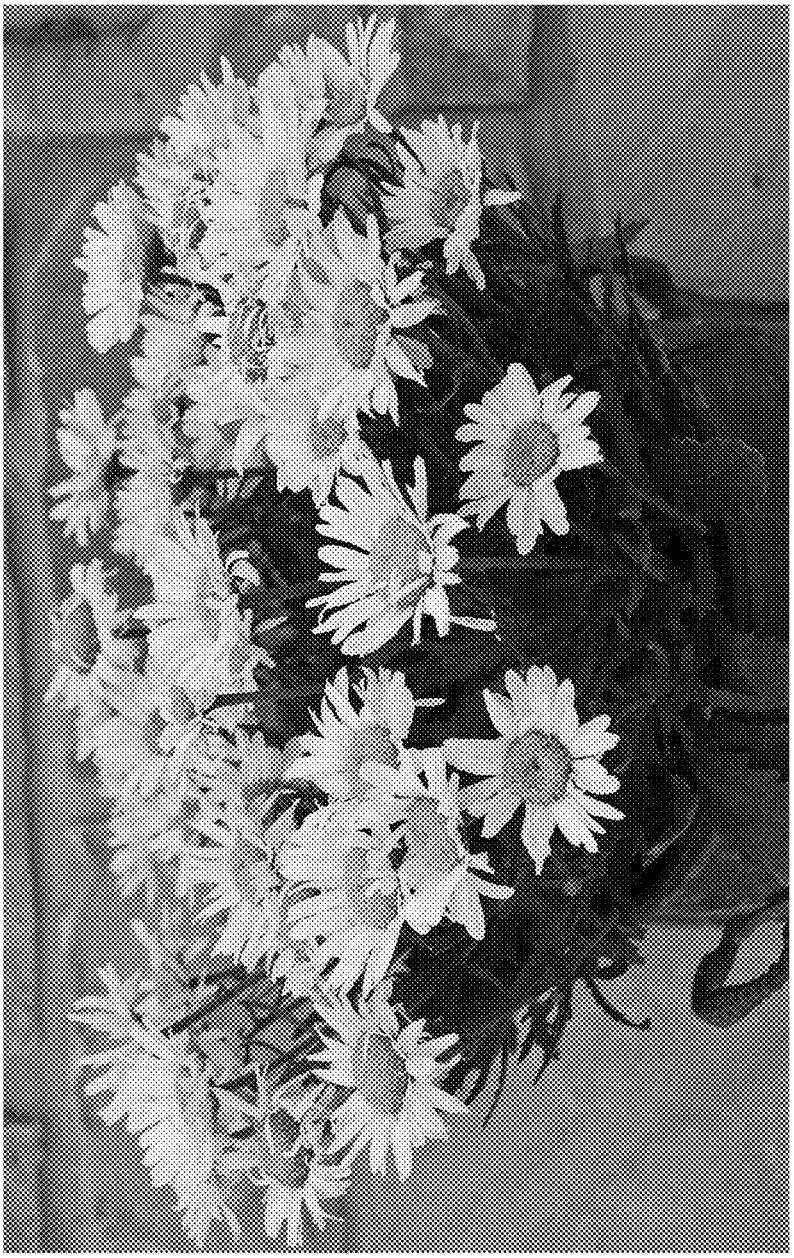

Botanical designation: *Leucanthemum* x *superbum*.
Cultivar denomination: 'SUNRIMAIAPY'.

CROSS-REFERENCED TO CLOSELY-RELATED APPLICATIONS

Title: *Leucanthemum* Plant Named 'SUNRIMAIZY'
Inventor: Scott C. Trees
Filed: Concurrently with the instant application

BACKGROUND OF THE INVENTION

The present invention relates to a new and distinct cultivar of *Leucanthemum* plant, botanically known as *Leucanthemum* x *superbum* and hereinafter referred to by the name 'Sunrimaiapy'.

The new *Leucanthemum* plant is a product of a planned breeding program conducted by the Inventor in Arroyo Grande, Calif. The objective of the breeding program is to create new *Leucanthemum* plants with a compact mounded habit, continuous flowering habit, numerous attractive inflorescences, no vernalization requirement for flowering, good garden performance and good winter hardiness.

The new *Leucanthemum* plant originated from an open-pollination in August, 2016 of *Leucanthemum* x *superbum* 'White Magic', disclosed in U.S. Plant Pat. No. 29,737, as the female, or seed, parent with an unknown selection of *Leucanthemum* x *superbum* as the male, or pollen, parent. The new *Leucanthemum* plant was discovered and selected by the Inventor as a single flowering plant from within the progeny of the stated open-pollination in a controlled environment in Arroyo Grande, Calif. in August, 2017.

Asexual reproduction of the new *Leucanthemum* plant by vegetative terminal cuttings in Arroyo Grande, Calif., since August, 2017 has shown that the unique features of this new *Leucanthemum* plant are stable and reproduced true to type in successive generations.

SUMMARY OF THE INVENTION

Plants of the new *Leucanthemum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunrimaiapy'. These characteristics in combination distinguish 'Sunrimaiapy' as a new and distinct *Leucanthemum* plant:

1. Relatively compact, upright and mounded plant habit.
2. Freely branching habit.
3. Strong flowering stems.
4. Early and freely flowering habit; long flowering period.
5. Large single-type inflorescences with white-colored ray florets and bright yellow-colored disc florets.
6. No vernalization requirement for flowering.
7. Good garden performance and winter hardiness.

Plants of the new *Leucanthemum* differ primarily from plants of the female parent, 'White Magic', in the following characteristics:

1. Plants of the new *Leucanthemum* are more compact and mounding than plants of 'White Magic'.
2. Plants of the new *Leucanthemum* are more freely branching than plants of 'White Magic'.
3. Leaves of plants of the new *Leucanthemum* are darker green in color than leaves of plants of 'White Magic'.
4. Plants of the new *Leucanthemum* flower more consistently and longer than plants of 'White Magic'.

Plants of the new *Leucanthemum* can be compared to plants of *Leucanthemum* x *superbum* 'Sunrimaizy', disclosed in a U.S. Plant Patent application filed concurrently. In side-by-side comparisons, plants of the new *Leucanthemum* differs from plants of 'Sunrimaizy' in the following characteristics:

1. Plants of the new *Leucanthemum* are shorter and have shorter internodes than plants of 'Sunrimaizy'.
2. Plants of the new *Leucanthemum* have smaller leaves than plants of 'Sunrimaizy'.
3. Plants of the new *Leucanthemum* have more inflorescences per plant than plants of 'Sunrimaizy'.
4. Plants of the new *Leucanthemum* have single-type inflorescences whereas plants of 'Sunrimaizy' have semi-double to double-type inflorescences.

Plants of the new *Leucanthemum* can be compared to plants of *Leucanthemum* x *superbum* 'Crazy Daisy', not patented. In side-by-side comparisons, plants of the new *Leucanthemum* differ from plants of 'Crazy Daisy' in the following characteristics:

1. Plants of the new *Leucanthemum* are more compact and mounding than plants of 'Crazy Daisy'.
2. Plants of the new *Leucanthemum* have single-type inflorescences whereas plants of 'Crazy Daisy' have double-type inflorescences.
3. Ray florets of plants of the new *Leucanthemum* are flatter and not as twisting as ray florets of plants of 'Crazy Daisy'.
4. Plants of the new *Leucanthemum* do not require vernalization for flowering whereas plants of 'Crazy Daisy' require vernalization for flowering.
5. Plants of the new *Leucanthemum* do not produce any detectable fragrance whereas plants of 'Crazy Daisy' produce the pungent and foul fragrance typical of *Leucanthemum* plants.

Plants of the new *Leucanthemum* can also be compared to plants of *Leucanthemum* x *superbum* 'Becky', not patented. In side-by-side comparisons, plants of the new *Leucanthemum* differ from plants of 'Becky' in the following characteristics:

1. Plants of the new *Leucanthemum* have darker green-colored leaves than plants of 'Becky'.
2. Plants of the new *Leucanthemum* have single-type inflorescences whereas plants of 'Becky' have semi-double type inflorescences.
3. Plants of the new *Leucanthemum* flower for a longer period of time plants of 'Becky'.
4. Plants of the new *Leucanthemum* do not require vernalization for flowering whereas plants of 'Becky' require vernalization for flowering.
5. Plants of the new *Leucanthemum* do not produce any detectable fragrance whereas plants of 'Becky' produce the pungent and foul fragrance typical of *Leucanthemum* plants.

BRIEF DESCRIPTION OF THE PHOTOGRAPHS

The accompanying colored photographs illustrate the overall appearance of the new *Leucanthemum* plant showing the colors as true as it is reasonably possible to obtain in colored reproductions of this type. Colors in the photographs may differ slightly from the color values cited in the detailed botanical description which accurately describe the colors of the new *Leucanthemum* plant.

The photograph on the first sheet (FIG. 1) is a side perspective view of a typical flowering plant of 'Sunrimaiapy' grown in a container.

Figure 2:
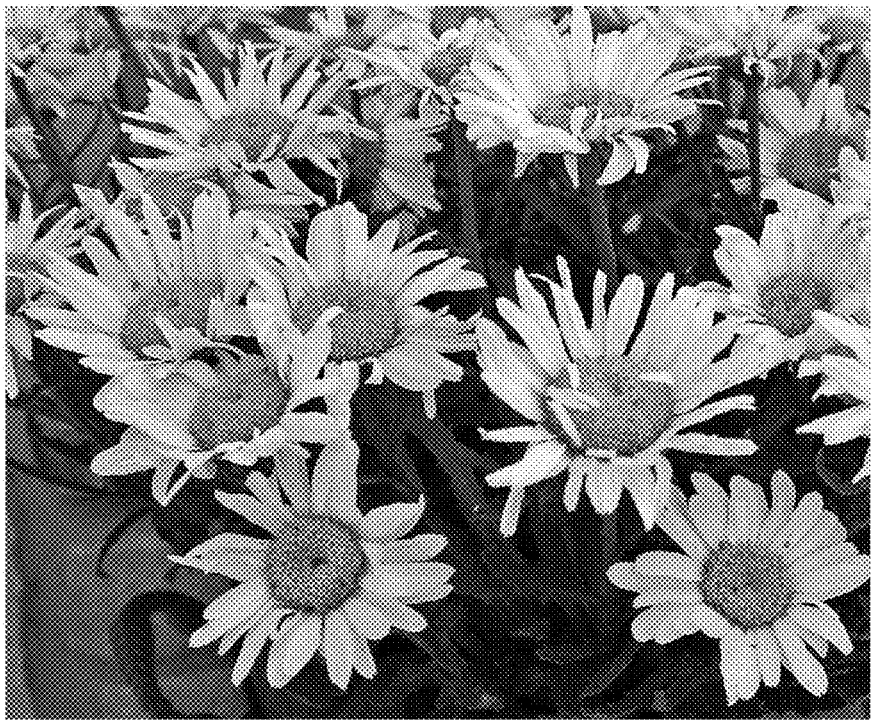

The photograph on the second sheet (FIG. 2) is a close-up view of a typical flowering plant of 'Sunrimaiapy'.

DETAILED BOTANICAL DESCRIPTION

The aforementioned photographs and following observations and measurements describe plants grown in 1.5-gallon containers during the summer in an outdoor nursery in West Chicago, Ill. and under cultural practices typical of commercial *Leucanthemum* production. During the production of the plants, day temperatures averaged 24° C. and night temperatures averaged 18° C. Plants were pinched two times and were 25 weeks old when the photographs and the description were taken. In the following description, color references are made to The Royal Horticultural Society Colour Chart, 2015 Edition, except where general terms of ordinary dictionary significance are used.

Botanical classification: *Leucanthemum* x *superbum* 'Sunrimaiapy'.

Parentage:

*Female, or seed, parent.*—*Leucanthemum* x *superbum* 'White Magic', disclosed in U.S. Plant Pat. No. 29,737.

*Male, or pollen, parent.*—Unknown selection of *Leucanthemum* x *superbum*, not patented.

Propagation:

*Type.*—Terminal vegetative cuttings.

*Time to initiate roots, summer.*—About eleven days at temperatures about 23° C. to 24° C.

*Time to initiate roots, winter.*—About 17 days at temperatures about 13° C. to 18° C.

*Time to produce a rooted young plant, summer.*—About 30 to 40 days at temperatures about 22° C.

*Time to produce a rooted young plant, winter.*—About 55 to 65 days at temperatures about 13° C. to 16° C.

*Root description.*—Medium in thickness, semi-fibrous; typically creamy white in color, actual color of the roots is dependent on substrate composition, water quality, fertilizer type and formulation, substrate temperature and physiological age of roots.

*Rooting habit.*—Freely branching, dense; rapid root system development.

Plant description:

*Plant and growth habit.*—Herbaceous perennial; relatively compact, upright and mounded plant habit; vigorous growth habit; moderate growth rate; freely branching habit with about ten to twelve primary branches each with numerous secondary branches developing per plant.

*Plant height.*—About 22.5 cm.

*Plant width.*—About 39.5 cm.

*Branch description.*—Length: About 20 cm. Diameter, at the base: About 8 mm. Internode length: About 1 cm. Strength: Strong. Aspect: Erect to about 45° from vertical. Texture and luster: Densely pubescent; semi-glossy. Color: Close to 137C and 144A to 144B.

*Leaf description.*—Arrangement: Alternate; simple. Length: About 8.75 cm. Width: About 3.25 cm. Shape: Oblanceolate to oblong. Apex: Acute. Base: Attenuate. Margin: Serrate. Texture and luster, upper and lower surfaces: Sparsely pubescent; slightly glossy. Venation pattern: Prominent midvein; pinnate. Color: Developing leaves, upper surface: Close to 147A. Developing leaves, lower surface: Close to 147B. Fully developed leaves, upper surface: Close to 147A; venation, close to 146A. Fully developed leaves, lower surface: Close to a blend of 147B and 146A; venation, close to 146A to 146B. Petioles: Length: About 5.3 cm. Width: About 3.5 mm to 4 mm. Texture and luster, upper surface: Smooth, glabrous; slightly glossy. Texture and luster, lower surface: Densely pubescent; slightly glossy.

Inflorescence description:

*Appearance*.—Large single-type inflorescences with ligulate- shaped ray florets and tubular disc florets; inflorescences held upright on strong peduncles, inflorescences face mostly upright; ray and disc florets develop acropetally on a capitulum.

*Fragrance*.—None detected.

*Flowering response*.—Plants begin flowering about twelve weeks after planting; plants flower continuously from the spring into the late summer in Northern Illinois.

*Postproduction longevity*.—Inflorescences maintain good substance for several weeks on the plant; inflorescences persistent.

*Quantity of inflorescences*.—Freely flowering habit, about 60 or more inflorescences develop per plant during the flowering season.

*Inflorescence size*.—Diameter: About 6.5 cm. Depth (height): About 1.5 cm. Disc diameter: About 2 cm.

*Receptacles*.—Height: About 5.5 mm. Diameter: About 1.2 cm. Color: Close to 144B.

*Inflorescence buds*.—Height: About 7.5 mm. Diameter: About 1 cm. Shape: Flattened sphere. Color: Close to 144A.

*Ray florets*.—Quantity per inflorescence: About 35 arranged in about one to two whorls. Length: About 2.5 cm. Width: About 7 mm. Shape: Ligulate. Apex: Acute, emarginate or praemorse. Base: Attenuate; fused at the base into a short tube. Margin: Entire; not undulate. Aspect: Mostly flat to slightly twisting. Texture and luster, upper and lower surfaces: Smooth, glabrous; not rugose; matte. Color: When opening and fully opened, upper surface: Close to 157D; fused base, close to 144A; color does not change with subsequent development. When opening and fully opened, lower surface: Close to NN155D; fused base, close to 144A; color does not change with subsequent development.

*Disc florets*.—Quantity per inflorescence: About 342 massed at the center of the receptacle arranged in numerous whorls. Length: About 8 mm. Diameter: Proximally, about 1 mm and distally, about 1.5 mm. Shape: Fused tubular with apices free. Apex: Acute, five-pointed. Texture and luster, inner and outer surfaces: Smooth, glabrous; slightly glossy. Color, when opening and fully opened, inner surface: Apex: Close to 12A. Mid-section: Close to 144A. Base: Close to 154D.

*Involucral bracts*.—Quantity per inflorescence: About 44 arranged in about two to three whorls. Length: About 1.1 cm. Width: About 2 mm. Shape: Oblong. Apex: Acute with obtuse tendencies. Base: Fused to the base of the receptacle. Margin: Entire, membraneous. Texture and luster, upper and lower surfaces: Smooth, glabrous; somewhat glossy. Color, upper and lower surfaces: Close to 144A.

*Peduncles*.—Length: About 20 cm. Diameter, at the base: About 8 mm. Strength: Strong. Aspect: Upright to about 45° from vertical. Texture and luster: Densely pubescent; semi-glossy. Color: Close to 137C and 144A to 144B.

*Reproductive organs*.—Androecium: Present on disc florets only. Quantity per floret: Five per disc floret. Filament length: About 3 mm. Filament color: Close to 145C to 145D. Anther shape: Roughly oblong. Anther length: Less than 1 mm. Anther color: Close to 10A. Pollen amount: None observed. Gynoecium: Present on ray and disc florets. Quantity per floret: One. Pistil length: About 4 mm. Stigma diameter: Less than 1 mm. Stigma shape: Bi-parted. Stigma color: Close to 12A to 12B. Style length: About 3 mm. Style color: Close to 154D. Ovary color: Close to 145C.

*Seeds and fruits*.—To date, seed and fruit development have not been observed on plants of the new *Leucanthemum*.

Pathogen & pest resistance: To date, plants of the new *Leucanthemum* have not been observed to be resistant to pathogens and pests common to *Leucanthemum* plants.

Garden performance: Plants of the new *Leucanthemum* have been observed to have good garden performance, no requirement for vernalization and to tolerate wind and rain, to suitable for USDA Hardiness Zones 5 to 11.

It is claimed:

1. A new and distinct *Leucanthemum* plant named 'Sunrimaiapy' as illustrated and described.

* * * * *